| United States Patent [19] | [11] | 4,210,768 |
|---|---|---|
| Swift | [45] | Jul. 1, 1980 |

[54] NICKEL SILICATE HYDROGENATION PROCESS

[75] Inventor: Harold E. Swift, Gibsonia, Pa.

[73] Assignee: Gulf Research and Development Company, Pittsburgh, Pa.

[21] Appl. No.: 936,245

[22] Filed: Aug. 24, 1978

[51] Int. Cl.$^2$ .......................... C07C 5/02; C07C 5/14
[52] U.S. Cl. ................................. 585/250; 585/259; 585/270; 585/276
[58] Field of Search ............................ 260/667, 683.9; 208/143; 585/270, 276, 250, 259

[56] References Cited

U.S. PATENT DOCUMENTS

| 3,859,370 | 1/1975 | Carter et al. | 260/667 |
| 3,865,895 | 2/1975 | Robson | 260/683.9 |
| 4,022,810 | 5/1977 | Kobylinski et al. | 260/449.6 M |

*Primary Examiner*—Veronica O'Keefe

[57] ABSTRACT

A process for hydrogenating hydrocarbons which comprises reacting a hydrocarbon with hydrogen in contact with a layered complex nickel silicate catalyst which has been reduced in a hydrogen atmosphere, oxidized in an atmosphere containing molecular oxygen and then again reduced in a hydrogen atmosphere.

10 Claims, No Drawings

NICKEL SILICATE HYDROGENATION PROCESS

BACKGROUND OF THE INVENTION

1. Field of the Invention

This invention relates to a process for hydrogenating hydrocarbons which comprises reacting a hydrocarbon with hydrogen in contact with a layered complex nickel silicate catalyst which has been reduced in a hydrogen atmosphere, oxidized in an atmosphere containing molecular oxygen and then again reduced in a hydrogen atmosphere.

2. Description of the Prior Art

Layered complex metal silicate catalysts are known and have been used, for example, to convert carbon monoxide and hydrogen to methane, as in U.S. Pat. No. 4,022,810 to Kobylinski et al. Surface properties of hydrogen reduced metal silicates have been described by Kibby et al in Journal of Catalysis 42, 350–359 (1976), pages 350 to 359.

SUMMARY OF THE INVENTION

I have found that certain layered complex metal silicate catalysts, defined hereinafter, can be used for hydrogenating hydrocarbons and their activity and longevity greatly extended, provided such catalysts are first reduced in a hydrogen atmosphere, oxidized in an atmosphere containing molecular oxygen and then again reduced in a hydrogen atmosphere.

The hydrogenation catalyst used herein is a layered complex metal silicate composition characterized as having repeating units of the structural formula:

$$[(1-x)Ni^{+2} + xMg^{+2}]_3(OH)_4Si_2O_5 \cdot wH_2O,$$

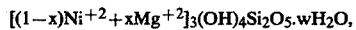

wherein x is a number from 0 to 0.6, preferably from 0 to 0.4, most preferably 0, this number expressing the atomic fraction of the metals nickel and magnesium, and w is a number from 0 to 4.

The catalyst can be prepared in many ways. Thus, a nickel salt alone, or in combination with a magnesium salt, such as nickel carbonate, nickel chloride, nickel acetate, a hydrated nickel oxide and the corresponding magnesium salts, are mixed with a source of silica, such as silicic acid (polysilicic acid) or sodium silicate. The molar ratio of the total metal salt used, as metal, to $SiO_2$ can be in the range of about 1.60:1 to about 2.0:1, preferably about 1.8:1 to about 1.9:1. To this mixture there is then added water to give a mol ratio of water to metal salt plus $SiO_2$ in the range of about 25:1 to about 150:1, preferably in the range of about 50:1 to about 100:1. A mineralizing agent, such as ammonium hydrogen fluoride, in an amount ranging from a mol ratio of $NH_4HF_2$ to metal salt plus $SiO_2$ in the range of about 0.01:1 to about 1.5:1, preferably in the range of about 0.02:1 to about 0.08:1, can also be added to the mixture to aid in the crystallization of the metal silicate catalyst. The reaction mixture is heated at a temperature of about 200° to about 375° C., preferably about 250° to about 325° C., and a pressure of about 225 to about 3200 pounds per square inch gauge (about 15.8 to about 225.3 kilograms per square centimeter), preferably about 370 to about 1750 pounds per square inch gauge (about 26 to about 123 kilograms per square inch centimeter), while stirring, for about two to about 24 hours, preferably about three to about eight hours. The reactor is then cooled to ambient (room) temperature and pressure and filtered to recover the solid contents thereof. The solids can then be oven dried at ambient pressure and a temperature of about 80° to about 250° C., preferably about 100° to about 200° C., for about two to about 24 hours, preferably about eight to about 12 hours. The catalyst recovered will have the structural formula defined hereinabove.

In order to greatly increase the activity and longevity of the above catalyst for use in hydrogenating hydrocarbons, it is essential that the catalyst first be reduced in a hydrogen atmosphere, then oxidized in an atmosphere containing molecular oxygen and then finally reduced again in a hydrogen atmosphere. The first and final hydrogenations can be effected by heating the catalyst at a temperature in the range of about 200° to about 600° C., preferably about 300° to about 550° C., for about one to about 24 hours, preferably about four to about 12 hours, while maintaining a hydrogen pressure thereon of about 15 to about 1000 pounds per square inch gauge (about one to about 70.4 kilograms per square centimeter), preferably about 50 to about 500 pounds per square inch gauge (about 3.5 to about 35.2 kilograms per square centimeter). The intermediate oxidation stage is conducted at a temperature of about 100° to about 600° C., preferably about 200° to about 550° C., for about two to about 24 hours, preferably about four to about 12 hours, with a gas containing from about two to about 90 volume percent molecular oxygen, preferably from about five to about 20 volume percent molecular oxygen. While the surface area of the total metal on the catalyst surface after a single-step hydrogenation treatment was on the order of about 20 to about 30 square meters per grams, after the hydrogenation, oxidation and hydrogenation sequences defined above, the total metal surface area was greatly increased to about 30 to about 50 square meters per gram, preferably about 40 to about 50 square meters per gram.

Any hydrocarbon, saturated or unsaturated, straight or branched-chained, compound capable of being hydrogenated can be hydrogenated using the catalyst defined hereinabove. Especially preferred hydrocarbons suitable as feed are aromatic compounds having from six to 14 ring carbon atoms, preferably from six to 12 ring carbon atoms, with or without functional groups, such as benzene, toluene, xylenes, ethylbenzene, styrene, naphthalene, anthracene, acenaphthene, phenanthrene, diphenyl, diphenyl methane, stilbene, bibenzyl, nitrobenzene, bromobenzene, benzyl chloride, etc.; olefinic and diolefinic compounds having from two to 60 carbon atoms, preferably from two to 40 carbon atoms, with and without functional groups, such as ethylene, n-butene, isoprene, butadiene, piperylene, cyclopentene, cyclopentadiene, dicyclopentadiene, octene-1, decene-1 (and oligomeric products thereof), crotonic acid, linoleic acid, ricinoleic acid, vinyl chloride, acrylonitrile, cyclohexene, etc.; acetylic compounds having from two to 10 carbon atoms, preferably from two to six carbon atoms, with and without functional groups, such as acetylene, 1-butyne, 1-chloro-4-penten-2 yne, etc. The hydrogenation can be a batch operation or a continuous operation at temperatures on the order of about 5° to about 500° C., preferably about 50° to about 400° C. and a hydrogen pressure of about 50 to about 5000 pounds per square inch gauge (about 3.5 to about 352 kilograms per square centimeter), preferably about 100 to about 1000 pounds per square inch gauge (about seven to about 70.4 kilograms per square centimeter). In a batch operation the residence time can be about 0.1 to about 36 hours, preferably about 0.5 to about 24 hours. In a continuous operation a liquid weight hourly space velocity (weight of hydrocarbon charge per weight of catalyst per hour) of about 0.25 to about 20, preferably about 0.5 to about 4.0.

DESCRIPTION OF PREFERRED EMBODIMENTS

A specific layered complex nickel silicate catalyst was prepared as follows. Into a ten-gallon autoclave there was added 343.6 grams of nickel carbonate in two gallons of water and 93.6 grams of SiO$_2$ in the form of polysilicic acid. This mixture was stirred and heated at a temperature of 300° C. for four hours, generating an autogeneous pressure of 1240 pounds per square inch gauge (87.3 kilograms per square centimeter). Upon completion of the reaction, the autoclave and its contents were cooled to room temperature, filtered to recover the solids therein and the solids so recovered were oven dried at room pressure and a temperature of 150° C. for eight hours.

The X-ray powder diffraction pattern of the catalyst is shown below in Table I.

TABLE I

| d (A.) | I |
|--------|---|
| 7.50   | s. |
| 4.50   | m. |
| 3.67   | s. |
| 2.58   | m. |
| 2.46   | m. |
| 2.10   | w. |
| 1.725  | w. |
| 1.545  | m. |
| 1.320  | w. |
| 1.300  | w. |

The sample was submitted for a surface area measurement by the BET method and the material was found to have a surface area of about 139 square meters per gram.

The solids, which were formed to 10-20 mesh granular particles, were then reduced in hydrogen, using a gas hourly space velocity of 300 and a pressure of 250 pounds per square inch gauge (17.6 kilograms per square centimeter) and a temperature of 420° C. over a period of 16 hours. The catalyst bed was cooled to 200° C. and a pressure of 15 pounds per square inch gauge (~1 kilogram per square centimeter) and then flushed with nitrogen. Next the catalyst was heated in an atmosphere containing 10 volume percent molecular oxygen and the rest molecular nitrogen for eight hours at 200° C. at 15 pounds per square inch gauge (~1 kilogram per square centimeter). Three grams of this catalyst was then charged to a high pressure reactor and heated to 450° C. While maintaining the pressure on the catalyst at 15 pounds per square inch gauge (~1 kilogram per square centimeter), hydrogen was passed over the catalyst at a gas hourly space velocity of 300 for a period of six hours.

A sample of the catalyst taken from the reactor at this stage was found to have a nickel surface area of about 50 square meters per gram as determined by an oxygen chemesorption technique. This is an exceptionally high nickel surface area.

Following this treatment with hydrogen, a liquid feed was pumped over the catalyst at 200° C. The feed consisted of 17.1 mol percent benzene, 75.9 mol percent cyclohexane, as diluent, and 7.0 mol percent sulfur in the form of thiopene. The feed was purposely made up with a large amount of sulfur in order to accelerate the study of the effect of this contaminant in the feed on the ability of the catalyst to maintain its hydrogenation capability. The feed was charged at the rate of 8.8 pounds per pound of catalyst per day. The hydrogen pressure in the reactor during the run was maintained at 250 pounds per square inch gauge (17.6 kilograms per square centimeter). This test was conducted similarly with additional hydrogenation catalysts. The product stream was monitored for benzene breakthrough of 1000 parts per million. The results are set forth below as Example I in Table II.

A second experiment was conducted wherein the specified layer complex nickel silicate catalyst was oven dried at room pressure and a temperature of 150° C. for eight hours. The solids, which were formed to 10-20 mesh granular particles were charged to the high pressure reactor and heated to 450° C. while maintaining the pressure on the catalyst at 15 pounds per square inch gauge (~1 kilogram per square centimeter), hydrogen was passed over the catalyst at a gas hourly space velocity of 300 for a period of six hours at 450° C. Following this a liquid feed was pumped over the catalyst the same as in Example I. The performance of this catalyst (Example II) is also given in Table II. It is evident that the reoxidation of the catalyst after initial hydrogen reduction greatly improves its activity, as shown by Example I.

TABLE II

| Catalyst | Weight Per Cent Nickel on Catalyst | Pounds of Benzene Processed Per Pound of Catalyst Before Benzene Breakthrough of More than 1000 PPM |
|----------|-----|-----------|
| Example I | 45 | 0.29-0.31 |
| Example II | 45 | <0.01 |
| Example III (UOP H-4) | 20 | 0.01-0.02 |
| Example IV (Harshaw-0104) | 60 | 0.09-0.10 |
| Example V (Girdler G-87-RS) | 40 | 0.11-0.12 |
| Example VI (CCI-C-46-6-02) | 45 | 0.04-0.05 |

Examples III to VI give results using nickel benzene hydrogenation catalysts which are available from catalyst vendors. The catalyst of Example III (UOP H-4) was obtained from Universal Oil Products, Ten UOP Plaza, Des Plaines, IL. The catalyst of Example IV (Harshaw-0104) was obtained from the Harshaw Chemical Company, 23800 Mercantile Road, P. O. Box 22126, Beachwood, OH. The catalyst of Example V (Girdler G-87-RS) and the catalyst of Example VI (CCI-C-46-6-02) were obtained from Girdler and CCI, respectively, which have been combined to form United Catalysts, Inc., P. O. Box 32370, Louisville, KY.

Table III below compares the surface properties of the catalyst prepared herein and used in Table II with the Harshaw-0104 catalyst.

TABLE III

| Catalyst | Surface Area, Square Meters/Gram | Pore Volume Milliliters/Gram |
|----------|------|------|
| Catalyst prepared herein (Ex. I) | 139 | 0.47 |
| Harshaw-0104 (Ex. IV) | 100-125 | 0.40 |

The above clearly shows the superiority of hydrogenating a hydrocarbon using the specific layered complex nickel silicate composition prepared herein over other well-known hydrogenation catalysts. More than twice the amount of benzene was hydrogenated using the catalyst prepared herein before 1000 parts of benzene appeared in the product stream when compared with the Harshaw and Girdler catalysts. With the remaining two catalysts even worse results were obtained. This is unusual, for although the Girdler catalyst contained only slightly less nickel, the Hawshaw catalyst contained much more. And, as Table III shows the difference could not be attributed to total surface area or pore volume, for there was little difference between the catalyst prepared herein and the Harshaw catalyst.

Obviously, many modifications and variations of the invention, as hereinabove set forth, can be made without departing from the spirit and scope thereof and, therefore, only such limitations should be imposed as are indicated in the appended claims.

We claim:

1. A process for hydrogenating hydrocarbons selected from the group consisting of aromatic compounds having from six to 14 ring carbon atoms, olefinic and diolefinic compounds having from two to 60 carbon atoms and acetylic compounds having from two to 10 carbon atoms which comprises reacting said hydrocarbon with hydrogen at a temperature of about 5° to about 500° C. and a pressure of about 50 to about 5,000 pounds per square inch gauge in contact with a layered complex nickel silicate catalyst characterized as having repeating units of the structural formula $$[(1-x)Ni^{+2}+xMg^{+2}]_3(OH)_4Si_2O_5 \cdot wH_2O,$$

wherein x is a number from 0 to 0.6 and w is a number ranging from 0 to 4, said catalyst having the following X-ray powder diffraction pattern:

| d(A.) | I |
| --- | --- |
| 7.50 | s. |
| 4.50 | m. |
| 3.67 | s. |
| 2.58 | m. |
| 2.46 | m. |
| 2.10 | w. |
| 1.725 | w. |
| 1.545 | m. |
| 1.320 | w. |

-continued

| d(A.) | I |
| --- | --- |
| 1.300 | w. | said catalyst having been treated, prior to said reaction, by reduction in a hydrogen atmosphere at a temperature of about 200° to about 600° C. and a pressure of about 15 to about 1,000 pounds per square inch gauge for a period of about one to about 24 hours, oxidation in an atmosphere containing molecular oxygen at a temperature of about 100° to about 600° C. for a period of about two to about 24 hours using a gas containing from about two to about 90 volume percent molecular oxygen and then again reduction in a hydrogen atmosphere at a temperature of about 200° to about 600° C. and a pressure of about 15 to about 1,000 pounds per square inch gauge for a period of about one to about 24 hours.

2. The process of claim 1 wherein x is a number from 0 to 0.4 and w is a number from 0 to 4.

3. The process of claim 1 wherein x is 0 and w is a number from 0 to 4.

4. The process of claim 1 wherein said reductions of said catalyst has been carried out at a temperature of about 300° to about 550° C. and a pressure of about 50 to about 500 pounds per square inch gauge for a period of about four to about 12 hours.

5. The process of claim 1 wherein said oxidation of said catalyst has been carried out at a temperature of about 200° to about 550° C. for a period of about four to about 12 hours using a gas containing from about five to about 20 volume percent molecular oxygen.

6. The process of claim 1 wherein the hydrocarbon is reacted with hydrogen at a temperature of about 5° to about 500° C. and a pressure of about 50 to about 5000 pounds per square inch gauge.

7. The process of claim 1 wherein the hydrocarbon is reacted with hydrogen at a temperature of about 50° to about 400° C. and a pressure of about 100 to about 1000 pounds per square inch gauge.

8. The process of claim 1 wherein said hydrocarbons are selected from the group consisting of aromatic compounds having from six to 12 ring carbon atoms, olefinic and diolefinic compounds having from two to 40 carbon atoms and acetylic compounds having from two to six carbon atoms.

9. The process of claim 1 wherein said hydrocarbon is an aromatic compound having from six to 14 ring carbon atoms.

10. The process of claim 1 wherein said hydrocarbon is an aromatic compound having from six to 12 ring carbon atoms.

* * * * *